United States Patent [19]

Incorvia et al.

[11] Patent Number: 5,534,192

[45] Date of Patent: *Jul. 9, 1996

[54] COMPOSITION AND METHOD FOR TREATING SUBSTRATES TO REDUCE ELECTROSTATIC CHARGE AND RESULTANT ARTICLE

[75] Inventors: Michael J. Incorvia, Lansdale; Stephen A. Fischer, Yardley, both of Pa.

[73] Assignee: Henkel Corporation, Plymouth Meeting, Pa.

[*] Notice: The term of this patent shall not extend beyond the expiration date of Pat. No. 5,478,486.

[21] Appl. No.: 392,712

[22] Filed: Feb. 22, 1995

Related U.S. Application Data

[63] Continuation-in-part of Ser. No. 154,665, Nov. 18, 1993, Pat. No. 5,478,486.

[51] Int. Cl.$^6$ .................. H05F 1/00; H05F 1/02
[52] U.S. Cl. .................. 252/500; 510/8.84; 57/901; 427/393.1; 427/393.5; 427/430.1; 427/434.2; 428/289; 428/290; 428/412; 428/423.1; 428/413; 428/474.4; 428/475.5; 428/480; 562/605; 564/291
[58] Field of Search .................. 252/8.6, 8.7, 8.8, 252/8.75, 500; 57/901; 524/910, 911; 428/289, 290, 412, 474.4, 475.5, 480, 423.1, 413; 427/394, 393.5, 430.1, 434.2; 562/605; 564/291

[56] References Cited

U.S. PATENT DOCUMENTS

| | | | |
|---|---|---|---|
| 2,759,019 | 8/1956 | Brown et al. | 564/96 |
| 2,809,990 | 10/1957 | Brown | 562/566 |
| 3,317,344 | 5/1967 | Mackey et al. | 430/527 |
| 4,006,064 | 2/1977 | Niederprum et al. | 205/290 |
| 4,089,804 | 5/1978 | Falk | 252/355 |
| 4,606,737 | 8/1986 | Stern | 252/8.8 |
| 4,873,020 | 10/1989 | Muggli | 252/355 |
| 5,219,493 | 6/1993 | Seshadri | 252/500 |

OTHER PUBLICATIONS

"Resistance and Static Behavior of Textile Surfaces", S. P. Hersh, Chapter 6, *Surface Characteristics of Fibers and Textiles*, Part 1, Marcel Dekker, Inc. (1975) [No Month].

*Primary Examiner*—Anthony Green
*Attorney, Agent, or Firm*—Ernest G. Szoke; Wayne C. Jaeschke; Real J. Grandmaison

[57] ABSTRACT

Antistatic agents and their use in processing textiles or formed plastic substrates. The antistatic agent comprises a compound having a fluorocarbon moiety and an ethoxylated quaternary ammonium moiety. The antistatic composition increases the electrolytic conductivity of textile or plastic materials treated therewith, thereby increasing the rate of electrostatic charge dissipation thereof. The coatings remain effective after exposure of the treated substrate to an aqueous environment.

24 Claims, No Drawings

COMPOSITION AND METHOD FOR TREATING SUBSTRATES TO REDUCE ELECTROSTATIC CHARGE AND RESULTANT ARTICLE

This application is a continuation-in-part application of prior application U.S. Ser. No. 08/154,665 filed on Nov. 18, 1993, now U.S. Pat. No. 5,478,486.

FIELD OF THE INVENTION

The present invention relates to antistatic agents and their use in textile and plastics processing.

BACKGROUND OF THE INVENTION

Electrostatic charge is the result of electrification of an object such that the charge is confined to the object. Friction between two surfaces in close contact typically gives rise to electrostatic charge or static electricity.

Textiles and plastics generally have low conductivity and dissipate charge at a relatively low rate. While it has been proposed to attenuate electrostatic charge build-up on textile and plastic materials by reducing its rate of generation, friction is inherent in many plastics and textile processing operations, particularly the latter, and cannot be substantially reduced. Consequently, increasing the rate of electrostatic charge dissipation of a textile or plastic material by increasing its electrolytic conductivity through the application of internal or external antistatic agents is commonly used as a means of controlling electrostatic build-up in such materials.

External or surface antistatic agents are directly applied as a coating to the surface layer of a textile or formed plastic substrate, typically dissolved or suspended in a suitable vehicle, such as water or another solvent. Internal antistatic agents are commonly used in formed plastic substrates and are physically mixed or blended with the resin mass prior to the forming operation, e.g., spinning, drawing, molding or the like, so as to be uniformly distributed throughout the body of the finished product, including the surface layer. Internal antistatic agents generally provide a longer lasting electrostatic charge dissipative effect.

Various chemicals have been proposed for use as antistatic agents, including, by way of example, long-chain amines, amides and quaternary ammonium salts; esters of fatty acids and their derivatives; sulfonic acids and alkyl aryl sulfonates; polyoxyethylene derivatives; polyglycols and their derivatives; polyhydric alcohols and their derivatives; and phosphoric acid derivatives.

Treatment of polyester and nylon fabrics with antistatic agents has been shown to reduce soiling. Static-prone plastic articles, such as packaging materials, that are treated with antistatic agents resist accumulation of dust and thus are more attractive for packaging of consumer products. Moreover, static charged plastic packaging and other plastic products have the potential to cause damage to semiconductor chips and constitute a possible explosion hazard in areas where flammable gases are used.

Ideally, surface antistatic agents used in textile and plastics processing are stable and not transient. That is to say, an amount of antistatic agent sufficient to provide effective electrostatic charge dissipation is retained on the surface of the coated substrate, whether textile or plastic, until processing is complete. Such processing often involves exposure of the treated textile or plastic to an aqueous environment, which tends to reduce the amount of antistatic agent present on the treated surface, thus diminishing its static dissipative effect. The use of stable antistatic agents offers the advantage of obviating repeated application of the antistatic agent to the static-prone substrate during processing.

Antistatic agents are also used for enhancing the receptivity of plastic surfaces to electrostatically applied coatings, e.g., in automobile production. See, for example, U.S. Pat. No. 5,219,493. In this application also, it is desirable that the antistatic agent resists removal when exposed to an aqueous rinse or wash liquid.

SUMMARY OF THE INVENTION

It is an object of the present invention to provide an antistatic agent capable of effectively dissipating electrostatic charge from a static-prone object treated therewith.

It is a further object of this invention to provide an antistatic agent for internal or external application to textile and plastic substrates.

It is another object of this invention to provide an antistatic agent providing a relatively long lasting electrostatic charge dissipative effect to substrates treated therewith, even after exposure of the treated substrate to an aqueous environment, such as aqueous rinse or wash liquid.

It has surprisingly been found that the above objects are achievable by means of the antistatic agent of the present invention which comprises a compound of the formula $(Q-L-R)_d-X$, wherein Q represents a straight or branched, saturated or unsaturated fluorine-containing aliphatic radical, L represents a linkage selected from the group consisting of ester, ether, amide or alkylene amine linkages, R represents a straight or branched alkylene-oxyalkylene or a straight or branched alkylene-poly(oxyalkylene) group, and d is 1 or 2, and, when d is 1, X represents at least one quaternary amine-forming group of the formula

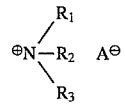

and, optionally, a tertiary amine-forming group of the formula

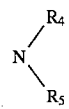

and, when d is 2, X represents a quaternary amine-forming group of the formula

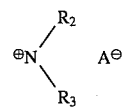

and, optionally, a tertiary amine-forming group of the formula

N—R$_5$ wherein $R_1$ and $R_4$ independently represent $$-(CH_2-CH-O)_f-Z,$$
$$\qquad\quad\;|$$
$$\qquad\quad R_a$$

Z being H, Q or $$\quad\; O$$
$$\quad\;\|$$
$$-C-Q,$$

f being an integer from 1 to 50, $R_2$ represents a $C_1-C_4$ alkyl group, $R_3$ and $R_5$ independently represent a straight or branched, saturated or unsaturated $C_6-C_{22}$ aliphatic group, $R_a$ represents H or $CH_3$, and A represents an organic or inorganic anion.

The reaction mixture that results from preparation of the aforesaid compound is applicable, as is, for antistatic treatment of various substrates. The resultant composition thus contains unreacted starting materials if present in stoichiometric excess, as well as the medium in which the reaction is conducted, the latter component serving to facilitate uptake of the antistatic agent by a static-prone substrate. One or more additional components, such as solvents, may be included in the resultant composition, e.g., to assist in solubilizing the compound, or in drying of the composition on the treated substrate. It is an advantage the present invention that isolation and recovery of the antistatically active agent from the reaction mixture is not required.

The present invention also provides a method for dissipating electrostatic charge on a static-prone substrate by incorporating into the substrate, either internally or externally, the antistatic agent of the invention in an amount effective to impart to the substrate a surface resistivity value in the range of from about $10^6$ to about $10^{12}$ ohms, a 90% electrostatic charge decay time of 10 seconds or less, or both.

Also in accordance with the present invention, there are provided articles of manufacture including textile, thermoplastic and thermoset substrates which are treated with the antistatic agent of the invention and effectively dissipate static electricity.

The antistatic agent and method of the invention may also be used to advantage for imparting a desired level of surface conductivity to formed plastic articles, such as automobile bumper parts, for electrostatically applied coating materials, resulting in good adhesion of the coating material to the treated article.

DETAILED DESCRIPTION OF THE INVENTION

As used herein, "antistatic agent" refers to a substance, or mixture of substances, taken up by a material, either internally or externally, to make the material static dissipative. The term "static-prone" refers to substrates that are susceptible to development of electrostatic charge, due to the way in which they are processed, or otherwise.

The antistatic composition of the invention is the product of a chemical reaction between a compound comprising a fluorocarbon radical with a polyalkoxylated quaternary ammonium compound and, optionally, a polyalkoxylated tertiary amine.

The reaction product preferably comprises an ester formed by the reaction of at least one straight or branched, saturated or unsaturated fluoroaliphatic carboxylic acid and a hydroxyl-substituted, alkoxylated quaternary ammonium compound. Alternatively, however, the ester may be the product of the reaction of a fluoroalcohol with an alkoxylated quaternary ammonium compound having one or more substituent carboxyl groups.

The antistatic reagent may also be prepared with an amide or alkylene amine linkage coupling the fluoroaliphatic group to the alkylene-oxyalkylene or alkylene-poly(oxyalkylene) groups, as the case may be. An amide linkage may be formed, for example, by reacting a suitable polyalkoxylated quaternary ammonium compound with ethyleneimine, or N-alkylated derivatives thereof, according to the equation:

$$R'OH + H_2C-NR\infty-CH_2 \rightarrow R'O-(CH_2)_2-NHR'',$$

wherein R' is, e.g., the residue of a polyalkoxylated quaternary ammonium compound and R" is hydrogen or a $C_1-C_4$ alkyl group. The resulting product is reacted in turn with a fluorocarboxylic acid, e.g., of the formula $C_qF_{2q+1}-COOH$, to yield an antistatic compound of the formula $$\qquad\qquad\qquad\qquad O$$
$$\qquad\qquad\qquad\qquad \|$$
$$R'O-(CH_2)_2-NR''-C-C_qF_{2q+1},$$

wherein R' and R" are as defined above, and q represents an integer from 1–17. Alternatively, the amide-linked antistatic compound may be prepared by reacting a fluoroalcohol with an ethyleneimine or derivative, as described above, with the resultant product being reacted with an alkoxylated quaternary ammonium compound having one or more substituent carboxyl groups. An alkylene amine linkage may be formed by reacting, e.g., a halogenated derivative of a polyalkoxylated quaternary ammonium compound with a primary amine according to the equation:

$$R'Cl + NH_2R'' \rightarrow R'NHR'' + HCl$$

wherein R' and R" are as previously defined. The resulting product is caused to react with a fluoroalkylated olefin, preferably an alpha-olefin, of the general formula $$H_2C=CH-C_qF_{2q+1}$$

to yield an antistatic compound of the formula $$R'R''N-(CH_2)_2-C_qF_{2q+1},$$

wherein R', R" and q are as previously defined.

Ether compounds of the type mentioned above may be prepared by fluorinated "capping" of hydroxyl-terminated, polyalkoxylated quaternary ammonium compounds with tetrafluoroethylene oxide or heptafluoropropylene oxide, according to procedures known in the art.

The fluorocarbon-containing compound is preferably of the formula $(C_qF_{2q+1})-COOH$, wherein q represents an integer from 1 to 17. Representative examples of such acids include perfluoro-acetic, propionic, butyric, pentanoic, hexanoic, heptanoic, octanoic, nonanoic and decanoic acids. The perfluorocarboxylic acids may contain mixtures of various chain lengths, depending upon their method of manufacture, and the use of such mixtures is within the scope of this invention.

Suitable hydroxyl-substituted, polyalkoxylated quaternary ammonium compounds for use in forming the antistatic composition of the invention include those of the formula

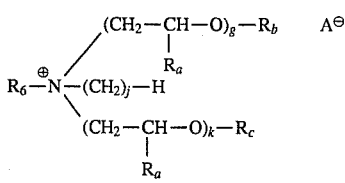

wherein $R_a$ represents H or $CH_3$, g and k may be the same or different and are each integers from 1 to 50, j is an integer from 1 to 4, $R_6$ represents a straight or branched, saturated or unsaturated $C_6$–$C_{22}$ aliphatic group, $R_b$ and $R_c$ independently represent H, straight or branched alkylene primary amine or straight or branched alkylene secondary amine, and A is an organic or inorganic anion, preferably halide, sulfate, lower alkyl sulfate or the like.

Particularly preferred hydroxyl-substituted, polyalkoxylated quaternary ammonium compounds are those of the formula

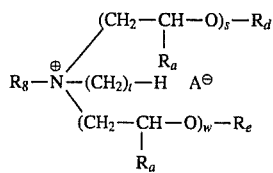

wherein $R_a$ is as previously defined, s and w may be the same or different and are each integers from 2–16; t is 1 or 2; $R_8$ represents a straight or branched, saturated or unsaturated $C_6$–$C_{18}$ aliphatic group, $R_d$ and $R_e$ independently represent H or

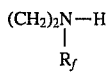

wherein $R_f$ is H or a $C_1$–$C_4$ alkyl group; A represents an anion selected from the group consisting of halide, sulfate and lower alkyl sulfate.

Examples of the preferred quaternary ammonium salts are ethyl bis(polyethoxyethanol) tallow ammonium salt, methyl bis(polyethoxy ethanol) coco ammonium salt, polyethoxy coco ether amine, diethylsulfate ammonium salt.

Most preferred are ethyl bis (polyethoxyethanol) tallow ethyl sulfate ammonium salt, available from Witco Corporation, under the trademark Variquat® 66 and methyl bis(polyethoxy ethanol) coco ethoxylated chloride ammonium salt, available from Witco Corporation under the product designation Variquat® K-1215.

Alkoxylated tertiary fatty amines of the formula

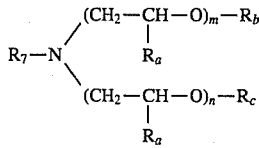

wherein $R_a$, $R_b$ and $R_c$ are as defined hereinabove, m and n are each integers from 1 to 50, preferably 2–16, which may be the same or different, $R_7$ represents a straight or branched, saturated or unsaturated, $C_6$–$C_{22}$ aliphatic group, preferably $C_6$–$C_{18}$, may optionally be included as reactants forming the antistatic composition of the invention, in combination with quaternary ammonium salts of the type described above. Variquat 66®, for example, comprises both hydroxyl-substituted, ethoxylated tertiary fatty amines and hydroxyl-substituted ethoxylated quaternary ammonium salts.

The alkoxylated tertiary fatty amines, when present, are typically of the formula

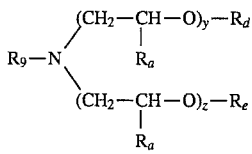

wherein $R_a$, $R_d$, and $R_e$, are defined above, Y and z may be the same or different and are nominally 8; $R_9$ represents a straight or branched, saturated or unsaturated, $C_6$–$C_{18}$ aliphatic group.

The tertiary amine reactants, having 2–16 repeating alkoxy units as indicated in the above formula, are characterized in product information provided by the manufacturers as nominally having eight repeating alkoxy units.

The antistatic compositions of the invention are prepared by known synthesis procedures, using conventional reaction conditions, as will be exemplified below. The progress of the reaction may be monitored, if desired, by standard analytical techniques, e.g., infra-red spectroscopy. The resulting reaction mixture may contain at least one of (i) the above-described fluorine containing acid; (ii) the above-described quaternary ammonium compound; and (iii) the above-described tertiary amine, each in unreacted form.

Although the resulting reaction mixture can advantageously be applied, as is, to static-prone substrates, various additives may be included in the reaction mixture to impart certain desirable properties to the resultant composition. The selection of appropriate additives will depend to some extent on the manner in which the antistatic agent is incorporated into the substrate. Additives may include solvents, e.g., isopropanol, surfactants such as ethoxylated nonylphenol (Trycol®6974, available from Henkel Corporation), and the like. The appropriate amount of any specific additive to be included in the antistatic composition of the invention may readily be determined on the basis of routine testing.

The antistatic composition may be applied to natural or synthetic textile materials or mixtures of natural and synthetic materials, e.g., nylon, rayon, acetate, rayon-cellulosic materials such as cellulose acetate-propionate, cellulose-butyrate, cotton, linen, jute, ramie, wool, mohair and glass, e.g., fiberglass and fiberglass insulation. The textile materials may take virtually any form, including individual fibers, yarns, woven materials such as fabrics, cloth, carpets, rugs and upholstery and non-woven materials such as felts, bats and mats. In the case of fiberglass strand or fiberglass insulation, the composition may be applied externally as a finish or as part of a sizing composition.

The plastic substrates to which the antistatic compositions of the invention may be beneficially incorporated include, for example, nylon (polyamide), polycarbonate, polyphenylene oxide, polyester, polyolefins and the like, and blends thereof with various other compatible resins.

Representative examples of suitable thermoplastic materials which have been treated using the antistatic composition of the invention are a polyester/polyether (Lomod®, Ashland Chemical Company), a nylon/polyester (Bexloy®, available from E.I. DuPont de Nemours) and a polyurethane (Bayflex®, available from Mobay Chemical). Commercial sheet molding compound, composed, for example, of a polyester filled with calcium carbonate and chopped glass fibers has also been treated with the antistatic composition described herein.

Examples of thermoset materials which may be treated with the antistatic composition of the invention include linear polyethylene, thermosetting alkyd, polyester and epoxy resins.

Incorporation of the antistatic composition into any given substrate will depend on the manner of manufacturing the substrate and may include surface application via padding, immersing, roller coating, spray coating and the like. The composition may also be blended with resinous materials which thereafter undergo various forming operations, e.g., extrusion or molding to yield the finished substrate. Of course, formed substrates may also be surface coated. For textile materials, the preferred form of application is by immersion, i.e., running the textile substrate through a bath of the antistatic composition. The appropriate mode of application may be selected by those skilled in the art in view of the overall dimensions or geometrical configuration of the surface to be treated. In any case, the mode of application should be one which causes a reasonably uniform thickness of the antistatic composition to be deposited on the treated surface. For flat surfaces, such as sheet or strip material, this may usually be accomplished most readily through the use of rollers or squeegees. The application temperature of the composition may vary over a wide range, but is preferably from 5° to 50° C.

Coating thickness may vary from as little as a monolayer to any desired thickness, although generally no advantage is achieved by thickness greater than about 20 microns, while the cost of the treatment is increased. Normally, the coating thickness for textile, thermoplastic or thermoset substrates to acquire an acceptable level of conductivity will be at least 0.2 microns. In operation, processing variables will normally be determined based upon the desired coating thickness to be obtained.

Any excess antistatic agent is typically removed from the treated substrate. The excess may be removed by a gentle water rinse, air knife blow drying, immersion in water (with or without agitation), air pressure or ultrasound. Drying may be carried out by, for example, circulating air, infra-red oven drying, or mechanical drying. While room temperature drying may be employed, it is preferable to use elevated temperatures to decrease the amount of drying time required.

Under normal operations, it is desirable to use elevated oven temperatures and warm air streams of velocity insufficient to disturb the wet film. From a practical standpoint, the drying temperature should be well below the softening point of the surface undergoing surface treatment.

Surfaces treated in accordance with the present invention are characterized by a surface resistivity of between about $10^6$ ohms and about $10^{12}$ ohms, about 90% electrostatic charge decay time of 10 seconds or less, or both. Devices for measuring resistivity or electrostatic charge decay time are commercially available from various sources and their use is exemplified herein below.

Static or charge dissipation is a function of the surface resistivity and capacitance of the material. Surface resistivity and capacitance are inversely related to the surface conductivity. In other words, the lower the values of surface resistivity and capacitance, the better the ability of an applied charge to dissipate to ground. Surface resistivity testing is complementary to electrostatic charge decay measurement tests which measure the time required for an applied charge to dissipate to a predetermined cut-off value. In electrostatic charge decay testing, the lower the time required for dissipation of the applied charge, the better the surface conductivity. Hence, low resistivity values will generally correlate with low static decay times.

Surfaces treated by the method of the invention will readily accept an electrostatically applied coating material, as will be exemplified below.

The following examples are provided to describe the invention in further detail. These examples, which set forth the best mode presently contemplated for carrying out the invention, are intended to illustrate and not to limit the invention.

EXAMPLE I

Preparation of Antistatic Composition

An antistatic composition in accordance with this invention was prepared by reacting 75 grams of ethyl bis(polyethoxyethanol) tallow ethyl sulfate ammonium salt with 25.5 grams of trifluoroacetic acid in the presence of anhydrous $MgSO_4$ (8 grams) in a 200 ml round bottom reaction vessel equipped with a mechanical stirrer. No solvent was used in conducting the reaction. A small amount of $H_2SO_4$ (approximately 0.4 grams) was added as a catalyst. The reaction was heated at 100° C. for 45 minutes. The reaction temperature was then raised to 150° C. for 30 minutes. The $MgSO_4$ in the mixture settled to the bottom of the reaction vessel. The reaction mixture was filtered through Whatman 5 qualitative filter paper to obtain a clear amber liquid, having a specific gravity of 1.1–1.2 grams/ml.

The reaction was followed by infrared spectroscopy. The product exhibited the convergence of bands about 950 and 915 $cm^{-1}$ to a band at 935 $cm^{-1}$ with a weak shoulder at 920 $cm^{-1}$. There was also a convergence of a band at 700 $cm^{-1}$ and its shoulder at 690 $cm^{-1}$ into a single sharp band at 700 $cm^{-1}$. An intensification of bands at 855, 780 and 735 $cm^{-1}$ was also observed. The 1020 $cm^{-1}$ band shifts/loses intensity to a new band at 1040 $cm^{-1}$. Intensity changes in the 1260 $cm^{-1}$ band are difficult to assign, but in general, it appears to lose intensity.

Other antistatic compositions in accordance with this invention can be prepared following the general procedure described above, but substituting a longer chain perfluoroaliphatic acid for trifluroacetic acid and/or quaternary ammonium compounds, such as methyl bis(polyethoxyethanol) coco ethoxylated chloride ammonium salt or Emerstat® 6660A (polyethoxy coco ether amine diethyl sulfate ammonium salt), for the quaternary ammonium salt exemplified herein.

The reaction described immediately above may be carried out in the presence of a solvent, if desired. Thus, 100.2 grams of Variquat was dissolved in 151 grams of toluene and the solution was heated under nitrogen to approximately 110° C. for forty-five minutes. To the heated solution was added 34 grams of trifluoroacetic acid and heating was continued at 113°–115° C. for about three hours. A water-toluene azeotrope was distilled and collected. The residual toluene was vacuum stripped from the reaction mixture at 77 millibar and 40° C.

A $^{13}C$ analysis was performed on the resultant reaction mixture. The spectrum of trifluoroacetic acid exhibited a quartet centered at ~116 ppm due to the $CF_2$ carbon and another quartet at ~161 ppm attributable to the carbonyl carbon. This spectrum evidences a doublet of quartets for the carbonyl and $CF_2$ carbons which suggest that the reaction mixture contains both starting material (i.e., unreacted acid) as well as product. If it is assumed that the weaker quartet in the ~116 ppm region is attributable to product, the result is a 1:1 ratio between the $CF_2$ resonances from the product to that of the $CH_3$ carbon of the quaternary ammonium salt reactant. These data suggest the presence of a monoester of the acid and the quaternary ammonium salt reactant. Strong resonances observed in the 122–140 ppm region were due to toluene.

The solvent used in this reaction should be carefully selected to minimize loss of reactants, especially in the case of relatively low boiling compounds, such as trifluoroacetic acid.

EXAMPLE II

Surface Application of Antistatic Composition to Nylon Yarns and Stability Testing Nylon yarn samples were treated with the following five antistatic compositions of the present invention: (1) a reaction product of ethyl bis(polyethoxyethanol) tallow ethyl sulfate ammonium salt and heptafluorobutyric acid; (2) a reaction product of methyl bis(polyethoxyethanol) coco ethoxylated chloride ammonium salt and heptafluorobutyric acid; (3) a reaction product of ethyl bis(polyethoxyethanol) tallow ethyl sulfate ammonium salt and trifluoroacetic acid; (4) a reaction product of ethyl bis(polyethoxyethanol) tallow ethyl sulfate ammonium salt and nonadecafluorodecanoic acid; and (5) a reaction product of ethyl bis(polyethoxyethanol) tallow ethyl sulfate ammonium salt and perfluoroheptanoic acid. The treated yarn samples possessed satisfactory surface resistivities (log (R) in the range of 8 to 10), which were maintained after washing with water in the case of four of the five antistatic compositions (1–3 and 5).

The protocol for making the resistance measurements was analogous to that described in "Resistance and Static Behavior of Textile Surfaces" by S. P. Hersh, Chapter 6 in *Surface Characteristics of Fibers and Textiles*, Part 1, ed. by M. J. Schick; Marcel Dekker, Inc. (1975).

EXAMPLE III

External Application of Antistatic Composition to Nylon 6,6 Panels and Determination of Resistivity 4"×6" panels composed of Nylon 6,6 [supplied by Advanced Coating Technologies, Inc., Hillsdale, Mich.] were used to determine the static dissipative effect of a composition of the invention, measured in terms of surface resistivity.

The antistatic composition used in this example was prepared according to the procedure described in Example I, above.

Each of three nylon 6,6 test panels was separately treated with (1) the antistatic composition of the invention, (2) ethyl bis(polyethoxyethanol) tallow ethyl sulfate ammonium salt alone, and (3) an unreacted mixture of trifluoroacetic acid and ethyl bis(polyethoxyethanol) tallow ethyl sulfate ammonium salt, according to the following test procedure. The nylon 6,6 panels were initially rinsed with deionized water and wiped with isopropanol. After determining that the resistivity of the cleaned panels was greater than or equal to $10^{15}$ ohms/ square (ohms/□) one of the treating agents was swabbed onto the panel. The swabbed panel was heated to 120° F. for 10 minutes and any excess antistatic agent was wiped from the panel with Kimwipe® tissue until no visible traces of the agent remained. The wiped panel was rinsed under a running stream of deionized water for 10 seconds per treated side, then dried at 120° F. for 10 minutes.

Each set of panels was measured for surface resistivity at a specified relative humidity using a Milli-to-2 Wide Range Resistance Meter with an Electro-Tech Systems, Inc., Model 803A, surface/volume resistivity probe. The resistivity values measured twenty-four hours after treatment and storage at 45% relative humidity are set forth in the following table.

TABLE 1

| | |
|---|---|
| Ethyl bis(polyethoxyethanol) tallow ethyl sulfate ammonium salt esterified with $CF_3COOH$ | $6.9 \times 10^{12}$ ohms/square |
| Ethyl bis(polyethoxyethanol) tallow ethyl sulfate ammonium salt | $8.0 \times 10^{13}$ ohms/square |
| $CF_3CO_2H$/ethyl bis (polyethoxyethanol) tallow ethyl sulfate ammonium salt | $3 \times 10^{13}$ ohms/square |

The data in Table I show that the surface resistance improves when ethyl bis(polyethoxyethanol) tallow ethyl sulfate ammonium salt is esterified with trifluoroacetic acid. The poorest surface resistance recorded for the fluorinated ester was two-and-a-half times more conductive than the best surface resistance recorded in the case of either the ethyl bis(polyethoxyethanol) tallow ethyl sulfate ammonium salt alone or an unreacted mixture of ethyl bis(polyethoxyethanol) tallow ethyl sulfate ammonium salt and trifluoroacetic acid. The data show overlap at the two sigma—90% confidence level.

The results of the foregoing tests show that the surface resistivity of the Nylon 6,6 panels treated with the antistatic composition of the invention is improved and longer lasting, as compared to Nylon 6,6 panels treated with ethyl bis(polyethoxyethanol) tallow ethyl sulfate ammonium salt alone or a mixture of ethyl bis (polyethoxyethanol) tallow ethyl sulfate ammonium salt and trifluoroacetic acid.

EXAMPLE IV

Surface Treatment of Panels with Antistatic Agent of the Invention and Comparative Agents and Determination of Conductivity 4"×6" thermoplastic panels composed of either Lomod, Bexloy, or Bayflex and panels of two different automotive sheet molding compounds (SMC A & B) composed of polyester ester filled with calcium carbonate and chopped glass fibers were used as test substrates to determine the static dissipative effect of the antistatic compositions of the invention. The panels of sheet molding compound differed from one another with respect to surface roughness, by reason of the application of a surface modifying "low profile" agent to one of the panels.

Each panel was initially rinsed in tap water, towel dried, and immersed for 2 minutes in an aqueous solution of antistatic agent followed by immersion for 2 seconds in deionized water, a 30 second tap water spray rinse at 12 psi and oven drying at 120° F.

In carrying out this experiment, a panel of each substrate type was treated with the following: (1) a mixture composed of stearyl dimethylammonium ethyl sulfate which is sold by PPG/Mazer Chemicals under the trademark Larostat® 451 and potassium hydrogen phthalate, which is the subject of U.S. Pat. No. 5,219,493; (2) ethyl bis(polyethoxyethanol) tallow ethyl sulfate ammonium salt; (3) an antistatic composition of the invention comprising the reaction product of trifluoroacetic acid and ethyl bis(polyethoxyethanol) tallow ethyl sulfate ammonium salt; (4) an antistatic composition of the invention comprising the reaction product of heptafluorobutyric acid and ethyl bis(polyethoxyethanol) tallow ethyl sulfate ammonium salt; (5) methyl bis(polyethoxyethanol)

coco ethoxylated chloride ammonium salt; (6) an antistatic composition of the invention comprising the reaction product of trifluoroacetic acid and methyl bis(polyethoxyethanol) coco ethoxylated chloride ammonium salt; and (7) an antistatic composition of the invention comprising the product of the reaction of heptafluorobutyric acid and methyl bis (polyethoxy ethanol) coco ethoxylated chloride ammonium salt.

Conductivity of the treated panels was measured by electrostatic charge decay at a specified relative humidity using an electrostatic charge decay meter (Model 406C, Electro-Tech Systems, Inc., Glenside, Pa.) according to the following procedure. A five KV charge (either positive or negative) was applied to the panel, then the charge was allowed to dissipate to a prescribed percentage of the initial charge (in this case 90% charge dissipation). The time in seconds required for decay of the charge to the specified level was measured. Conductivity of the treated panels is inversely proportional to the time required for the prescribed electrostatic decay to occur.

The results of electrostatic charge decay measurements on the treated panels are set forth in the following Table II.

TABLE II

Decay Times* for Treated Thermoplastics

| Treating Agent | SMC A | SMC B | Lomod | Bexloy | Bayflex |
|---|---|---|---|---|---|
| 1 | 3.78 | RC | 0.10 | 21.2 | 10.0 |
| 2 | 5.05 | RC | 0.20 | 28.4 | 20.4 |
| 3 | 3.48 | RC | 0.15 | 22.4 | 1.19 |
| 4 | 1.58 | 13.99 | 0.12 | 12.28 | 0.28 |
| 5 | RC | RC | 0.08 | 26.4 | 9.51 |
| 6 | 6.91 | RC | 0.07 | 30.0 | 2.56 |
| 7 | 3.16 | RC | 0.08 | 15.8 | 0.34 |

*5 KV — 500 V decay times measured in seconds
RC = Residual Charge

The test results set forth in Table II indicate that the panels treated with the antistatic composition of the invention exhibit superior electrostatic charge decay as compared with the other agents tested.

EXAMPLE V

Effect of Varying the Chain Lengths of the Fluorine-Containing Constituents of the Antistatic Agent on Substrate Conductivity 4"×6" panels of the same substrates tested in Example IV, above, were used to determine the effect on conductivity of the treated panels resulting from varying the chain length of the fluorinated carboxylic acid constituent of the antistatic composition of the invention.

In carrying out this test, an untreated panel of each substrate type was used as a control.

A test panel of each substrate type was treated with (1) ethyl bis(polyethoxyethanol) tallow ethyl sulfate ammonium salt; (2) a reaction product of trifluoroacetic acid and ethyl bis(polyethoxyethanol) tallow ethyl sulfate ammonium salt; (3) a reaction product of heptafluorobutyric acid and ethyl bis(polyethoxyethanol) tallow ethyl sulfate ammonium salt; (4) a reaction product of perfluoroheptanoic acid and ethyl bis(polyethoxyethanol) tallow ethyl sulfate ammonium salt; (5) a reaction product of nonadecafluorodecanoic acid and ethyl bis(polyethoxyethanol) tallow ethyl sulfate ammonium salt; (6) methyl bis(polyethoxyethanol) coco ethoxylated chloride ammonium salt; (7) a reaction product of trifluoroacetic acid and methyl bis(polyethoxyethanol) coco ethoxylated chloride ammonium salt; and (8) a reaction product of heptafluorobutyric acid and methyl bis(polyethoxyethanol) coco ethoxylated chloride ammonium salt.

Conductivity of the treated panels was measured by electrostatic charge decay for a specific relatively humidity (R.H. of 50%) using an electrostatic charge decay meter in the manner described in Example IV, above.

The results of static decay measurements on the panels treated as described above are set forth in the following table.

TABLE III

| Treating Agent | SUBSTRATE* | | | | |
|---|---|---|---|---|---|
| | Bexloy | Lomod | Bayflex | SMC A | SMC B |
| Control | 21.2 | 0.10 | 10.0 | 3.78 | RC |
| 1 | 28.4 | 0.20 | 20.4 | 5.05 | RC |
| 2 | 22.4 | 0.15 | 1.19 | 3.48 | RC |
| 3 | 12.3 | 0.12 | 0.28 | 1.58 | 14.0 |
| 4 | 7.11 | 0.11 | 1.00 | 12.2 | RC |
| 5 | 1.08 | 0.17 | 2.56 | 11.6 | RC |
| 6 | 26.4 | 0.08 | 9.51 | RC | RC |
| 7 | 30.0 | 0.07 | 2.56 | 6.91 | RC |
| 8 | 15.8 | 0.08 | 0.34 | 3.16 | RC |

* 5 KV–500 V decay times measured in seconds
RC — Residual Charge

The test results set forth in Table III show that panels treated with the antistatic compositions formed from fluorocarbons of relatively greater chain length and quaternary ammonium salts of relatively longer chain hydrocarbons tend to impart higher conductivity (i.e., shorter decay times) to the treated panels.

EXAMPLE VI

Surface Treatment of Thermoplastic Substrate with Antistatic Agent Followed By Application of Electrostatic Coating A thermoplastic airbag cover (Izumi), measuring 4×5 inch, was used as a substrate to determine the effect of the antistatic agent of the invention on the conductivity of such a substrate and the adhesion of a subsequently applied electrostatic coating. The same substrate, which was not treated with the antistatic agent of the invention, was used as a control.

In carrying out the test, the substrate was treated with an antistatic agent resulting from the reaction of a quaternary ammonium ethyl sulfate salt mixture of 10 weight percent $CH_3CH_2N(CH_2CH_2OH)_3^{\oplus}$ and 90 weight percent $C_nH_{2n+1}OCH_2CH_2N(CH_2CH_3)(CH_2CH_2OH)_2^{\oplus}$ (Emerstat® 6660A) where n=12 to 14 with trifluoroacetic acid in a toluene solution to which a small amount of base material was added. The reaction product was distilled to remove a water-toluene azeotrope formed during the reaction.

An antistatic treatment bath was made up comprising 50 grams of the resultant antistatic agent, 50 grams isopropanol, 2 grams ethoxylated nonylphenol (Trycol® 6974) and 898 grams deionized water. The bath was heated to 125° F. to disperse the antistatic agent. The substrate was immersed in the treatment bath for 5 minutes, then spray rinsed for about 30 seconds at 10–15 psi with deionized water and oven dried for 5 minutes at 120° F.

Conductivity of the treated substrate was measured by electrostatic charge decay at a predetermined relative humidity (40%) using an electrostatic charge decay meter (Model 406C, Electro-Tech Systems, Glenside, Pa.) according to the following procedure. A 5 KV charge (either positive or negative) was applied to the substrate, then the charge was allowed to dissipate to the extent of 90% of the initial charge. The time in seconds required for decay of the charge to the 90% level was measured. Conductivity of the test panel is inversely proportional to the time required for the prescribed electrostatic decay to occur. For the treated substrate, the measured decay time was 0.5 seconds, indicating that the conductivity was maintained after aqueous rinse.

The treated substrate exhibited fair wrap around by a subsequent coating of enamel which was electrostatically applied to the substrate. By comparison, the untreated substrate exhibited no wrap around after electrostatic application of the same enamel coating.

While it is apparent that the various embodiments of the invention disclosed and exemplified are well suited to fulfill the above-stated objects, it will be appreciated that the invention is susceptible to modifications, variations and change without departing from the spirit of the invention, the full scope of which is delineated by the appended claims.

What is claimed is:

1. An antistatic agent of the formula $(Q-L-R)_d-X$, wherein Q represents a straight or branched, saturated or unsaturated perfluoroaliphatic radical, L represents a linkage selected from the group consisting of ester, ether, amide or alkylene amine linkages, R represents a straight or branched alkylene-oxyalkylene or a straight or branched alkylene-poly(oxyalkylene) group, and d is 1 or 2, and, when d is 1, X represents at least one quaternary ammonium group of the formula

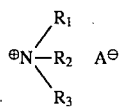

and, optionally, a tertiary amine-forming group of the formula

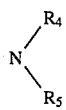

and, when d is 2, X represents a quaternary amine-forming group of the formula

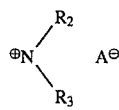

and, optionally, a tertiary amine-forming group of the formula

wherein $R_1$ and $R_4$ independently represent

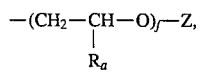

Z being H, Q or

wherein Q is as defined above, f being an integer from 1 to 50, $R_2$ represents a $C_1$–$C_4$ alkyl group, $R_3$ and $R_5$ independently represent a normal or branched, saturated or unsaturated $C_6$–$C_{22}$ aliphatic group, $R_a$ represents H or $CH_3$, and A represents an organic or inorganic anion.

2. An antistatic agent as claimed in claim 1 comprising an ester having as its reactive components at least one saturated perfluoroaliphatic carboxylic acid and at least one quaternary ammonium compound of the formula

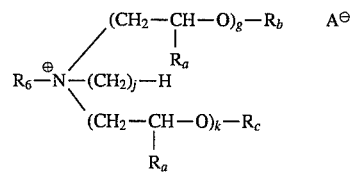

wherein $R_a$ is as previously defined, g and k may be the same or different and are each integers from 1 to 50, j is an integer from 1 to 4, $R_6$ represents a straight or branched, saturated or unsaturated $C_6$–$C_{22}$ aliphatic group, $R_b$ and $R_c$ independently represent H, straight or branched alkylene primary amine or straight or branched alkylene secondary amine, and A is an organic or inorganic anion, and, optionally, a tertiary amine of the formula

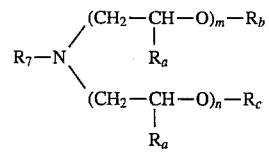

wherein $R_a$, $R_b$ and $R_c$ are as defined above, m and n may be the same or different and are each integers from 1 to 50 which may be the same or different, $R_7$ represents a straight or branched, saturated or unsaturated, $C_6$–$C_{22}$ aliphatic group; said antistatic agent further containing at least one of (i) said saturated perfluoroaliphatic carboxylic acid in unreacted form, (ii) said quaternary ammonium compound in unreacted form and, optionally, (iii) said tertiary amine in unreacted form.

3. An antistatic agent as claimed in claim 2 comprising an ester having as its reactive components at least one acid of the formula $(C_qF_{2q+1})$—COOH, wherein q represents an integer from 1–17; at least one quaternary ammonium compound of the formula

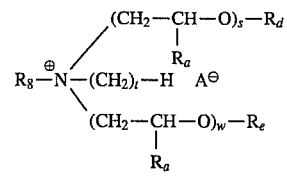

wherein $R_a$ is as previously defined, s and w may be the same or different and are each integers from 2–16, t is 1 or 2, $R_8$ represents a straight or branched, saturated or unsaturated $C_6$–$C_{18}$ aliphatic group, $R_d$ and $R_e$ independently represent H or

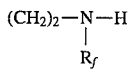

wherein $R_f$ is H or a $C_1$–$C_4$ alkyl group, A represents an anion selected from the group consisting of halide and lower alkyl sulfate; and at least one tertiary amine of the formula

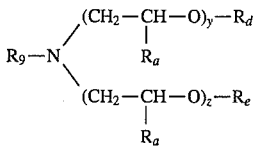

wherein $R_a$, $R_d$ and $R_e$ are as defined above, y and z may be the same or different and are nominally 8, $R_9$ represents a straight or branched, saturated or unsaturated, $C_6$–$C_{18}$ aliphatic group; and said antistatic agent further containing at least one of (i) said acid in unreacted form, (ii) said quaternary ammonium compound in unreacted form, and (iii) said tertiary amine in unreacted form.

4. An antistatic agent as claimed in claim 1 wherein said amide linkage has been formed by reacting a polyalkoxylated quaternary ammonium compound with ethyleneimine or a N-alkylated derivative of ethyleneimine, and then reacting the resulting product with a fluorocarboxylic acid of the formula $C_qF_{2q+1}$—COOH wherein q represents an integer from 1 to 17.

5. An antistatic agent as claimed in claim 1 wherein said amide linkage has been formed by reacting a fluoroalcohol with ethyleneimine or a N-alkylated derivative of ethyleneimine, and then reacting the resulting product with an alkoxylated quaternary ammonium compound having one or more substituent carboxyl groups.

6. An antistatic agent as claimed in claim 1 wherein said alkylene amine linkage has been formed by reacting a halogenated derivative of a polyalkoxylated quaternary ammonium compound with a primary amine, and then reacting the resulting product with a fluoroalkylated olefin of the formula $H_2C=CH-C_qF_{2q+1}$ wherein q represents an integer from 1 to 17.

7. A method for dissipating an electrostatic charge on a static-prone substrate selected from the group consisting of a textile substrate, a formed, thermoplastic substrate and a formed thermoset substrate, comprising the step of applying to said substrate an antistatic agent as claimed in claim 1 in an amount effective to impart to said substrate a surface resistivity value in the range of from about $10^6$ to about $10^{12}$ ohms, a 90% electrostatic charge decay time of 10 seconds or less, or both.

8. A method as claimed in claim 7 wherein said antistatic agent is applied to a textile substrate.

9. A method as claimed in claim 8 wherein said textile substrate is selected from the group consisting of nylon, rayon, acetate, cotton, wool, linen, and mixtures thereof.

10. A method as claimed in claim 7 wherein said substrate is selected from the group consisting of polycarbonate, polyamide, polyphenylene oxide, polyester, polyolefin, and mixtures thereof.

11. A method as claimed in claim 7, wherein said antistatic agent comprises an ester having as its reactive components at least one acid of the formula $(C_qF_{2q+1})$—COOH, wherein q represents an integer from 1–17; and at least one quaternary ammonium compound of the formula

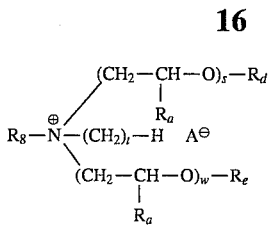

wherein $R_a$ is as previously defined, s and w may be the same or different and are each integers from 2–16, t is 1 or 2, $R_8$ represents a straight or branched, saturated or unsaturated $C_6$–$C_{18}$ aliphatic group, $R_d$ and $R_e$ independently represent H or

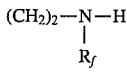

wherein $R_f$ is H or a $C_1$–$C_4$ alkyl group, A represents an anion selected from the group consisting of halide and lower alkyl; and at least one tertiary amine of the formula

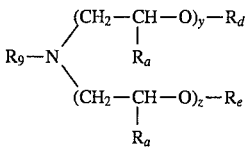

wherein $R_a$, $R_d$ and $R_e$ are as defined above, y and z may be the same or different and are each integers from 2–16, $R_9$ represents a straight or branched, saturated or unsaturated, $C_6$–$C_{18}$ aliphatic group; and said antistatic agent further containing at least one of (i) said acid in unreacted form, (ii) said quaternary ammonium compound in unreacted form, and (iii) said tertiary amine in unreacted form.

12. A method as claimed in claim 7 wherein said antistatic agent is applied to a surface of said substrate.

13. A method as claimed in claim 8 wherein said antistatic agent is applied to said substrate by passing said textile substrate through a bath comprising said antistatic agent.

14. A method as claimed in claim 7 wherein said antistatic agent is applied to a formed, thermoplastic substrate.

15. A method as claimed in claim 14 wherein an antistatic agent comprising an ester having as its reactive components at least one acid of the formula $(C_qF_{2q+1})$—COOH, wherein q represents an integer from 1–17; and at least one quaternary ammonium compound of the formula

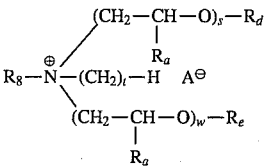

wherein $R_a$ is as previously defined, s and w may be the same or different and are each integers from 2–16, t is 1 or 2, $R_8$ represents a straight or branched, saturated or unsaturated $C_6$–$C_{18}$ aliphatic group, $R_d$ and $R_e$ independently represent H or

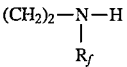

wherein $R_f$ is H or a $C_1$–$C_4$ alkyl group, A represents an anion selected from the group consisting of chloride and lower alkyl sulfate; and at least one tertiary amine of the formula

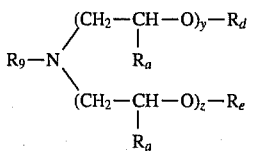

wherein $R_a$, $R_d$ and $R_e$ are as defined above, y and z may be the same or different and are each integers from 2–16, $R_9$ represents a straight or branched, saturated or unsaturated $C_6$–$C_{18}$ aliphatic group; and said antistatic agent further containing at least one of (i) said acid in unreacted form, (ii) said quaternary ammonium compound in unreacted form, and said tertiary amine in unreacted form is applied to said thermoplastic substrate.

16. A method as claimed in claim 15, wherein said antistatic agent is applied to a surface of said substrate.

17. A method as claimed in claim 7, wherein said antistatic agent is applied to a formed thermoset substrate.

18. A method as claimed in claim 17, wherein an antistatic agent comprising an ester having as its reactive components at least one acid of the formula $(C_qF_{2q+1})$—COOH, wherein q represents an integer from 1–17; and at least one quaternary ammonium compound of the formula

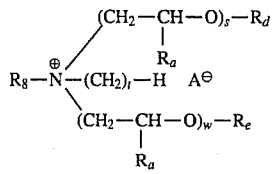

wherein $R_a$ is as previously defined, s and w may be the same or different and are each integers from 2–16, t is 1 or 2, $R_8$ represents a straight or branched, saturated or unsaturated $C_6$–$C_{18}$ aliphatic group, $R_d$ and $R_e$ independently represent H or

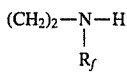

wherein $R_f$ is H or a $C_1$–$C_4$ alkyl group, A represents an anion selected from the group consisting of chloride and lower alkyl sulfate; and at least one tertiary amine of the formula

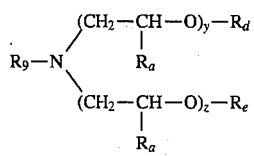

wherein $R_a$, $R_d$ and $R_e$ are as defined above, y and z may be the same or different and are each integers from 2–16, $R_9$ represents a straight or branched, saturated or unsaturated, $C_6$–$C_{18}$ aliphatic group; and said antistatic agent further containing at least one of (i) said acid in unreacted form (ii) said quaternary ammonium compound in unreacted form and (iii) said tertiary amine in unreacted form is applied to said thermoset substrate.

19. A method as claimed in claim 17, wherein said antistatic agent is applied to a surface of said substrate.

20. An article of manufacture comprising a substrate selected from the group consisting of a textile substrate, a formed, thermoplastic substrate and a formed, thermoset substrate having applied thereto the antistatic agent of claim 1.

21. An article of manufacture as claimed in claim 20, wherein an antistatic agent comprising an ester having as its reactive components at least one acid of the formula $(C_qF_{2q+1})$—COOH, wherein q represents an integer from 1–17; at least one quaternary ammonium compound of the formula

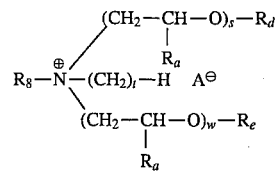

wherein $R_a$ is as previously defined, s and w may be the same or different and are each integers from 2–16, t is 1 or 2, $R_8$ represents a straight or branched, saturated or unsaturated $C_6$–$C_{18}$ aliphatic group, $R_d$ and $R_e$ independently represent H or

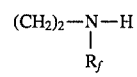

wherein $R_f$ is H or a $C_1$–$C_4$ alkyl group, A represents an anion selected from the group consisting of halide and lower alkyl sulfate; and a tertiary amine of the formula

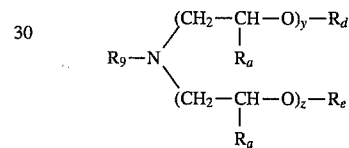

wherein $R_a$, $R_d$ and $R_e$ are as defined above, y and z may be the same or different and are each integers from 2–16, $R_9$ represents a straight or branched, saturated or unsaturated, $C_6$–$C_{18}$ aliphatic group; and said antistatic agent further containing at least one of (i) said acid in unreacted form, (ii) said quaternary ammonium compound in unreacted form, and (iii) said tertiary amine in unreacted form is applied to said substrate.

22. A composition comprising the product of the reaction between at least one straight or branched, saturated or unsaturated perfluoroaliphatic carboxylic acid and at least one quaternary ammonium compound of the formula

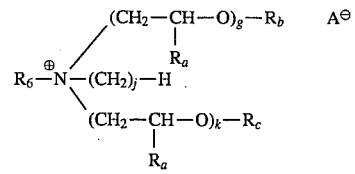

wherein $R_a$ represents H or $CH_3$, g and k may be the same or different and are each integers from 1 to 50, j is an integer from 1 to 4, $R_6$ represents a straight or branched, saturated or unsaturated $C_6$–$C_{22}$ aliphatic group, $R_b$ and $R_c$ represent H, straight or branched alkylene primary amine or straight or branched alkylene secondary amine, and A is an organic or inorganic anion, and, optionally, a tertiary amine of the formula

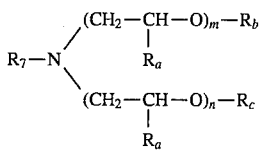

wherein $R_a$, $R_b$ and $R_c$ are as defined above, m and n may be the same or different and are each integers from 1 to 50 which may be the same or different, and $R_7$ represents a straight or branched, saturated or unsaturated, $C_6$–$C_{22}$ aliphatic group; and said antistatic agent further containing any of said acid, said quaternary ammonium compound, or said tertiary amine in unreacted form.

23. A composition as claimed in claim 22 which further includes a vehicle for application of said reaction product into a static-prone substrate.

24. A composition as claimed in claim 22 wherein said acid is of the formula $(C_qF_{2q+1})$—COOH, wherein q represents an integer from 1–17; said quaternary ammonium compound is of the formula

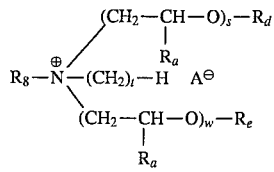

wherein $R_a$ is as previously defined, s and w may be the same or different and are each integers from 2–16, t is 1 or 2, $R_8$ represents a straight or branched, saturated or unsaturated $C_6$–$C_{18}$ aliphatic group, $R_d$ and $R_e$ independently represent H or

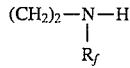

wherein $R_f$ is H or a $C_1$–$C_4$ alkyl group, A represents an anion selected from the group consisting of halide and lower alkyl sulfate; and said tertiary amine is of the formula

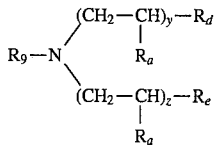

wherein $R_a$, $R_d$ and $R_e$ are as defined above, y and z may be the same or different and are each integers from 2–16, and $R_9$ represents a straight or branched, saturated or unsaturated, $C_6$–$C_{18}$ aliphatic group.

* * * * *

UNITED STATES PATENT AND TRADEMARK OFFICE
CERTIFICATE OF CORRECTION

PATENT NO. : 5,534,192
DATED : Jul. 9, 1996
INVENTOR(S) : Incorvia et al.

It is certified that error appears in the above-indentified patent and that said Letters Patent is hereby corrected as shown below:

In Col 4, line 14, "$R'OH + H_2C-NR\infty-CH_2 \rightarrow R'O-(CH_2)_2-NHR$", " should read -- $R'OH + H_2C-NR''-CH_2 \rightarrow R'O-(CH_2)_2-NHR''$, --.

In Col 16, line 20, claim 11, after "alkyl" please insert --sulfate--.

Signed and Sealed this

Third Day of March, 1998

Attest:

BRUCE LEHMAN

*Attesting Officer*     *Commissioner of Patents and Trademarks*